United States Patent [19]

Bontemps

[11] Patent Number: 5,297,694
[45] Date of Patent: Mar. 29, 1994

[54] DEVICE WITH CONSTANT MAGNETIC FIELD TO PRESERVE PERISHABLE SUBSTANCES

[76] Inventor: Raymond Bontemps, 5, Av. de La Grande Armee, 75116 Paris, France

[21] Appl. No.: 954,003

[22] Filed: Sep. 30, 1992

[30] Foreign Application Priority Data

Nov. 13, 1991 [FR] France .................. 91 13931

[51] Int. Cl.⁵ .............................. B65D 35/28
[52] U.S. Cl. .................... 220/666; 220/667; 220/DIG. 7; 215/1 C; 222/95; 222/103
[58] Field of Search ......... 215/1 C, 231; 220/230, 220/666, 667, 907, DIG. 7; 222/92, 93, 95, 103

[56] References Cited

U.S. PATENT DOCUMENTS 712,447 10/1902 Woolley .................. 220/230
4,981,238 1/1991 Wenmaekers .............. 222/103

Primary Examiner—Allan N. Shoap
Assistant Examiner—Nova Stucker
Attorney, Agent, or Firm—Kramer, Brufsky & Cifelli

[57] ABSTRACT

A container made of a substantially dielectric material adapted to contain and preserve a perishable substance, comprising:
a substantially elongated tubular portion defining an enclosure adapted to contain a perishable substance, the tubular portion being made from a flexible dielectric material, and defining an opening adapted to release said perishable substance through the opening by squeezing the tubular portion;
a first magnet coupled to an interior wall of the tubular portion and extending substantially the length of the tubular position;
a second magnet coupled to said interior wall of the tubular portion of a substantially opposite side of the tubular portion relative to the first magnet and facing the first magnetic defining a magnetic field between the first and second magnets; said magnetic field adapted to substantially encompass said perishable substance; and
a porous material located between the first and second magnets to prevent contact between the first and second magnets.

5 Claims, 4 Drawing Sheets

DEVICE WITH CONSTANT MAGNETIC FIELD TO PRESERVE PERISHABLE SUBSTANCES

DESCRIPTIVE SUMMARY

The present invention concerns a magnetic device with a parallel field that is applied to cream contained in jars or tubes. These substances are free, for the most part, of preservatives.

According to FIG. 1, the device is characterized by a hollow jar (1) containing the cosmetic cream free of essential preservatives.

At the bottom of this jar is placed a ferrite magnet (5) covered by the cosmetic cream, and another ferrite magnet (4) is coupled to a cover (2) by twisted plastic rods (6) which hold the magnet (4) on top of the cream. The magnet (4) descends in proportion to the level of the cream along an inclined rod constituting a rail.

The present invention is used in the cosmetological and pharmaceutical industry.

The present invention has for a subject a solid or flexible container in which an intense magnetic field is maintained by means of two ferrite magnets, one of which is placed in a sliding manner in a perishable substance so as to preserve the products throughout the duration of their use.

Up to the present time, the ability to preserve products, especially creams and milks, for a long duration by keeping them under the effect of a magnetic field has been known.

In fact, it has been observed according to a well known principle that any body, isolated particle, or molecule, regardless of the physical conditions and, in particular, temperature and pressure, manifests magnetic properties, i.e., has a certain reaction when it is immersed in a magnetic field. This effect is due to the nuclear spin of the molecules subjected to the magnetic field. The magnetic preservation capacity has been known for several years, and different devices and containers are known, notably in which static preservation magnets are incorporated.

Thus, containers of various forms contain within a double wall a calibrated magnet which is positioned with regard to another magnet so that the north-south axis and south-north axis are perpendicular in both the horizontal and vertical planes, with a number of magnets, typically at least four for each container, or more, depending upon the shape or size of the container in which the product to be preserved is placed.

This device has numerous disadvantages, notably:
 a weak and dispersed magnetic field, and
 a difficult implementation and adaptation to each container.

Moreover, the weakness of the magnetic field, and its dispersion makes the action of the magnetic properties ineffective when the substance has been partially consumed. In fact, the vacuum due to the absence of substance reduces the magnetic field and disperses the magnetic-field lines.

The present invention permits elimination of these disadvantages by using two ferrite magnets, one of which is fixed, and the other of which follows progressively the level of the cream or ointment during its consumption.

This magnetic field is constantly maintained in the ointment or the cream and has a tendency to increase during the consumption of the preserved cosmetic product. This device notably permits presenting to the consumer cosmetic creams or ointments from which, in most cases, chemical preservatives which have been the origin of a certain toxicity for the user, have been eliminated. The action of the magnetic field advantageously replaces the chemical preservative.

The present invention is referred to as a novel device with constant magnetic field to preserve perishable substances and is characterized in that it comprises a container, jars or tubes made of dielectric material, equipped with two mobile ferrite magnets whose south-north magnetic poles are face to face. One of the magnets is glued or otherwise coupled to the bottom of the jar, and the other is placed under the cover by means of flexible plastic rods which are twisted, and keep the magnet face to face with the south-magnet surface opposite the magnet at the bottom of the jar, without ever touching it. Moreover, under the effect of the twisted plastic rods, a vertical gliding movement drives this magnet which, after screwing on the cover, will come to rest on the surface of the ointment in proportion to its use. The magnet suspended from the cover has a diameter close to the inner diameter of the jar so as to fit snug within the jar, and descends down to the upper surface of the ointment by means of a groove cut in the disk-shaped magnet. The magnet slides on an inclined rail adhered to the inner wall of the jar, keeping it from turning while descending the magnet slowly by screwing on the cover. A similar adaptation is applied in a tube containing an ointment or cream.

The present invention as characterized has numerous advantages, linked to the low cost of manufacture, the ease of use, and the adaptation to all types of jars or tubes.

The present invention will be better understood by means of the attached drawings which are created only as an example of a particular embodiment.

Thus, any device where the upper magnet is held by pins, for example, must be considered as being part of the present invention.

Figure 1:
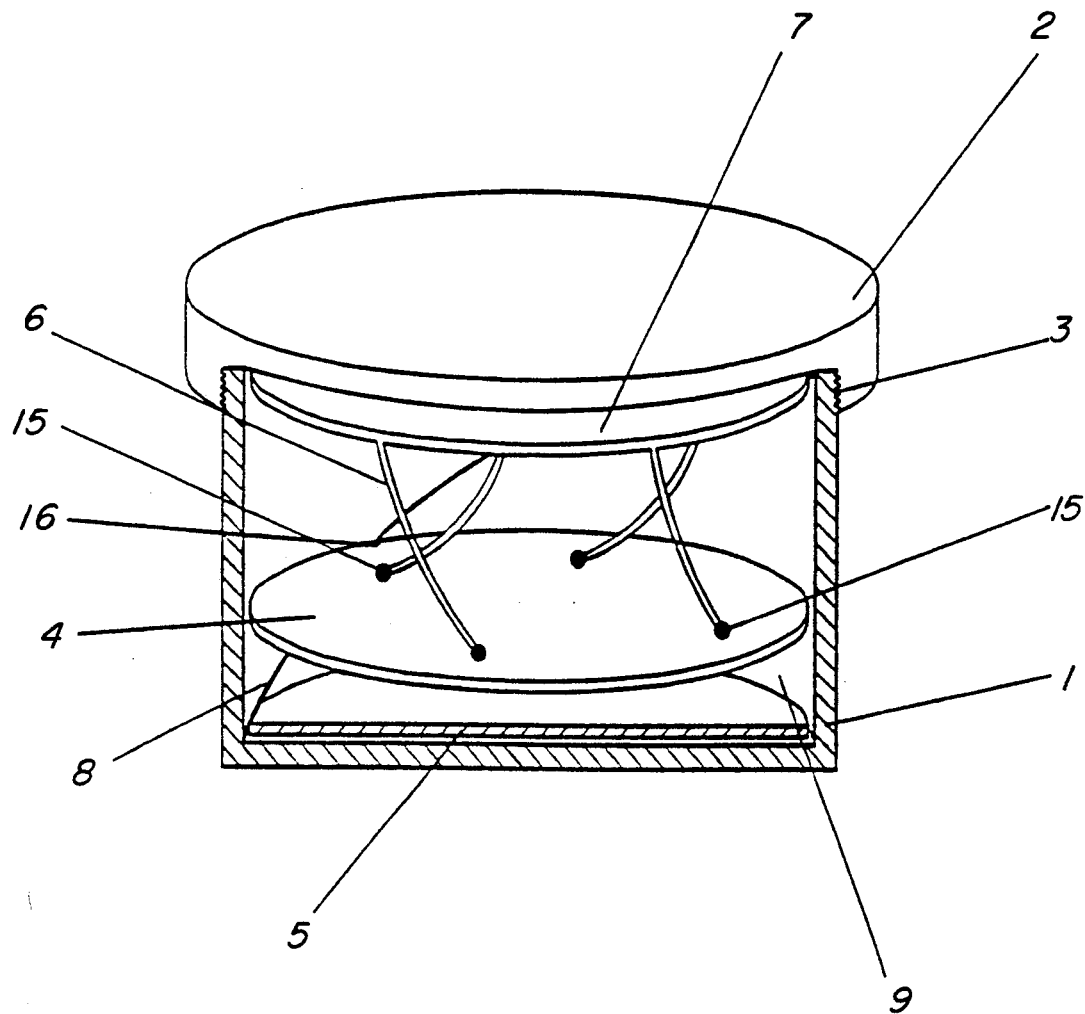
FIG. 1 illustrates a first embodiment of the present invention and represents a jar for cream drawn in section and shows the inside arrangement of the magnets.

FIG. 1 illustrates a round cream jar embodying the present invention drawn in section. This jar (1) is made of rigid plastic or glass, or even any other dielectric element, and contains cream (9). It is closed by a cover (2) which screws on at level (3). A disk of magnetized ferrite (5) presenting its north surface is glued onto the entire bottom surface of the jar. The other magnetized ferrite disk (4) presents its south face to magnet (5). The disk (4) is connected to cover (2) by means of flexible dielectric plastic rods (6) or tongue-like members, which are twisted in proportion to the extent the cover is screwed onto the jar. These flexible tongues (6) exert an extremely weak torque, and when they are folded back they apply a weak pressure on magnet disk (4) which rests on the surface of the ointment or cream (9). Flexible tongues (6) are attached to magnet (4) by gluing or soldering at points (15), and the other ends of tongues (6) are attached to the cover by means of a washer (7) which ensures the airtightness of the jar.

The magnet (4) descends in proportion to the level of the cream (9) and this descent is guided by a vertical and inclined or oblique rod (8) glued onto the inner walls of the jar (1). A notch (16) cut into the magnet (4) is engaged in this rail guide (8) in order to carry out its progressive descent.

This guide can advantageously be eliminated by using an oval-shaped jar. This arrangement is provided so as to prevent any circular or rotational movement of magnet (4) during screwing on of cover (2) of the jar and to prevent the magnet from being immersed in cream (9). In this hypothesis, a portion of the cream above magnet (4) would not be subjected to the magnetic field and thus would be subject to a defect in preservation.

Figure 2:
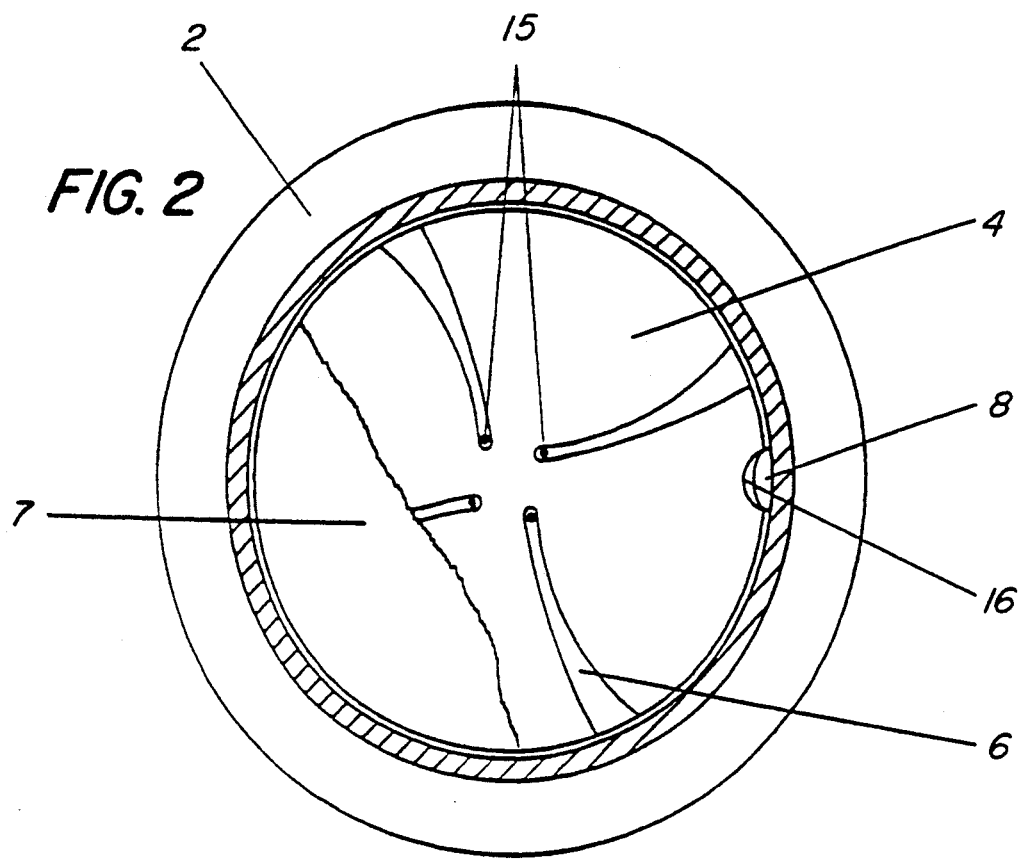
FIG. 2 is a cross-sectional view of the device of FIG. 1 and illustrates the attachment device for the upper magnet onto the flexible plastic rods, which are twisted, and the guiding grooves.

FIG. 2 is drawn in section and, viewed from above, illustrates the device for holding magnet (4) onto the cover and its arrangement in the jar.

The wall of jar (1) is made up of dielectric material covered with a threaded cap (2). The upper magnet (4) is attached to the sealing washer (7) which itself is made up in one piece with threaded cap (2).

The connection between washer (7) and magnet (4) is obtained by means of four flexible plastic rods (6) which are compressed in a twisted manner during screwing on of the cover. The profile of each of these rods is in an arc of a circle, of which one end is glued to washer (7) of cap (2), and the other to magnet (4).

These four rods shaped in the arc of a circle are made of flexible plastic of several millimeters in diameter and the profile of their drawing forms a deformable coil.

The other ends of these four rods converge toward the center of the cover without reaching it.

Each of these rods is soldered or glued at level (15) to magnet (4), and thus hold the magnet. This arrangement permits making the circular magnet (4) mobile around the diameter of the jar, tracing in its twisting the arc of a circle.

The circular magnet disk (4) is provided with a notch (16) which penetrates during the screwing of the jar into a rail (8) made up of an inclined rod (8) glued to the inside of the jar. In order to facilitate sliding, this rail can be slightly inclined with regard to the vertical axis of the jar, or can have a curved profile running from the top to the bottom of the jar.

During screwing of the jar, magnet disk (4) is placed so that notch (16) leans into or receives rail (8). During screwing of the cover, the disk slides along the rail down to the height of the cream level without undergoing rotation. The torque of plastic rods (6) induces a slight vertical pressure on magnet disk (4) without inducing the immersion of the latter into the cream. The lengths of plastic rods (6) are calculated and made so that magnet (4) cannot come into contact with magnet (5) placed at the bottom of the jar. The north-south magnetic field is maintained between the two magnets.

Figure 3:
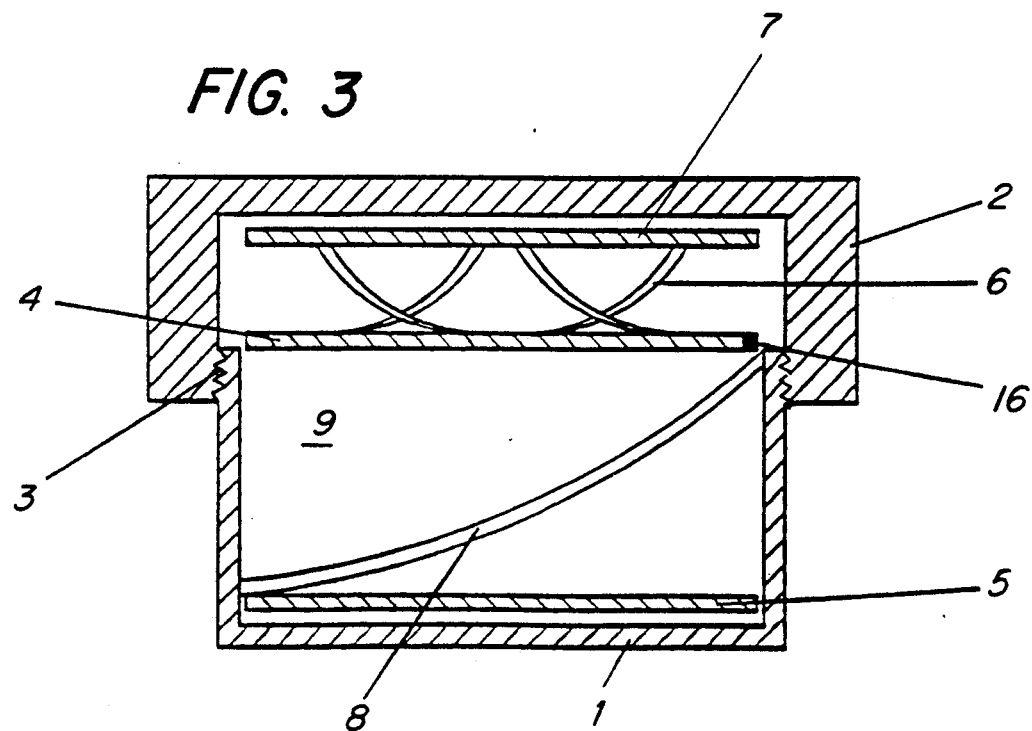
FIG. 3 is a cross-sectional view of the device of FIG. 1 when filled with cream, illustrating the flexible plastic rods folded up upon screwing on the cover.

FIG. 3 illustrates the closed jar (1) containing cream (9).

Cover (2) is lodged or threaded onto the jar at level (3). Magnet (5) is glued to the bottom of the jar. Upper magnet (4), whose magnetic pole is opposite to that of magnet (5), is placed on the surface of the cream. Twisted plastic rods (6) supporting magnet (4) are turned sideways and are flattened out during screwing without forcing the magnet into the cream. Magnet (4) is a circular airtight disk preventing penetration of the cream towards the cover. Moreover, washer (7) assures the seal of the assembly and serves to support magnet (4) by means of the flexible twisted plastic rods (6).

Figure 4:
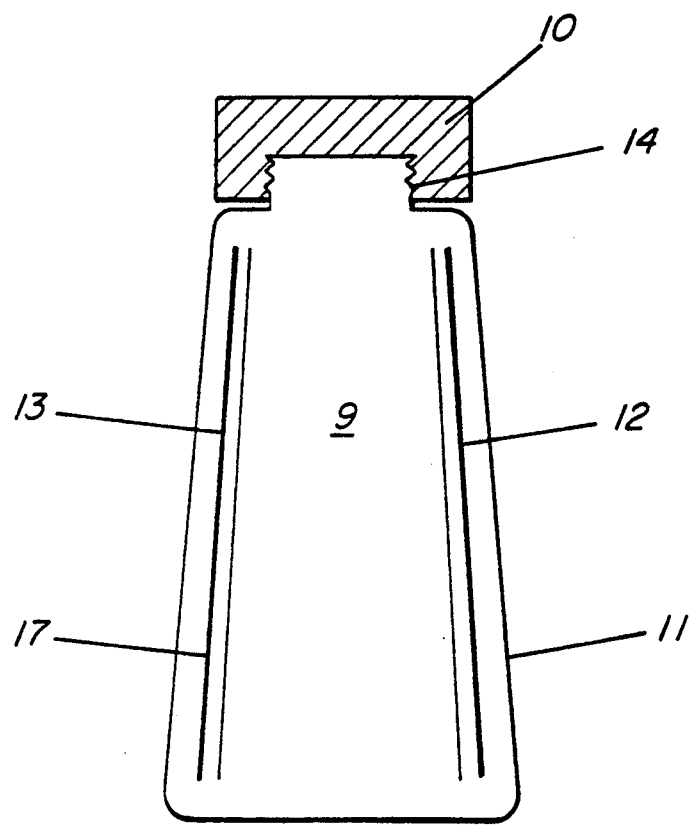
FIGS. 4 and 5 illustrate another embodiment of the present invention adapted to a tube of cream.
Figure 5:
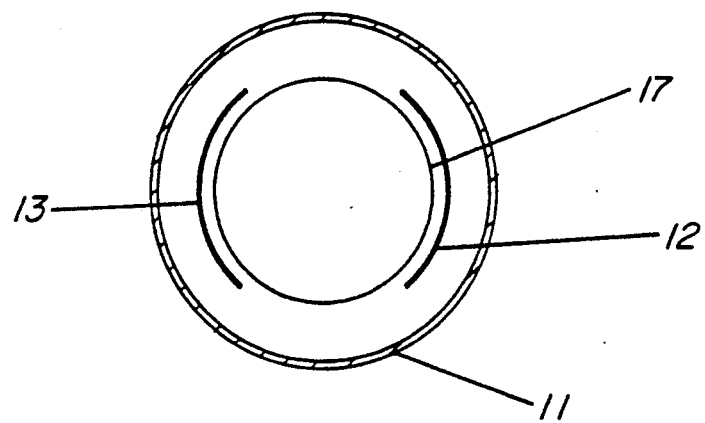

FIGS. 4 and 5 illustrate a variation of the system of the present invention adapted for the tube containing cream.

The tube (11) is of flexible plastic sealed by a threaded cap (10) at level (14). Two magnets (12) and (13), whose north-south faces are opposed and extend in substantially the longitudinal direction of the tube, create a magnetic field on the cream. These two magnets are isolated by means of film (17) made up of either gauze or a fine porous plastic film. This film can constitute, for example, a bag in which cream (9) is contained. Magnets (12) and (13) whose N and S signs are opposed, induce a magnetic field sufficient to store the cosmetic substances without preservative. During use by pressing the flexible tube, the gauze or film will eliminate any risk of contact which would destroy the magnetic field of preservation.

Figure 6:
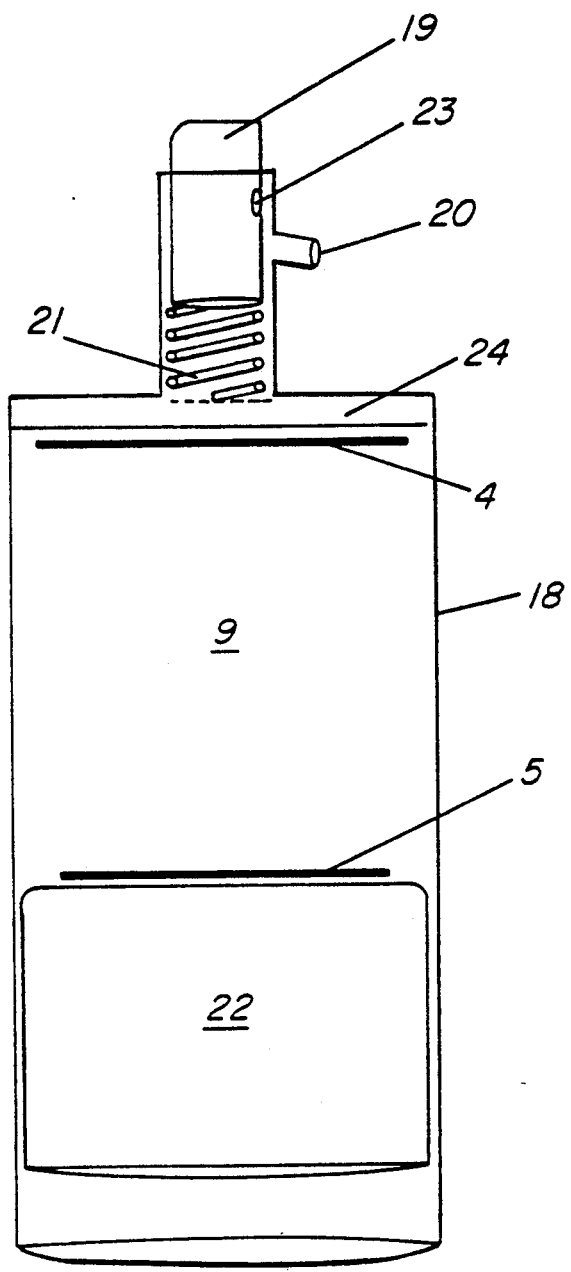
FIG. 6 illustrates another embodiment of the present invention incorporated within a flask whose bottom is mobile.

FIG. 6 illustrates another embodiment of the present invention in a flask (18) whose bottom (22) is mobile in order to permit a compression of the perishable ointment or substance (9). This compression permits inducing the extraction of the ointment or substance through opening (20) made up in one piece with flask (18). Magnets (4) and (5) are face to face, positioned under cover (24) and on the mobile inner bottom (22) of the flask. When pressure is effected on push button (19), openings (23) and (20) are aligned. Cover (24), in communication with the reserve supply of perishable substance or ointment (9), permits bringing up the product through openings (23) and (20). At rest, the push button returns to its closed position by means of a spring (21).

As the flask is emptied, bottom (22) is raised in a piston fashion, and the magnetic field is maintained permanent by means of magnet (5) which is mobile and adhered to the bottom (22).

I claim:

1. A container made of a substantially dielectric material adapted to contain and preserve a perishable substance, comprising:

a substantially elongated tubular portion defining an enclosure adapted to contain a perishable substance, the tubular portion being made from a flexible dielectric material, and defining an opening adapted to release said perishable substance through the opening by squeezing the tubular portion;

a first magnet coupled to an interior wall of the tubular portion and extending substantially the length of the tubular position;

a second magnet coupled to said interior wall of the tubular portion of a substantially opposite side of the tubular portion relative to the first magnet and facing the first magnet defining a magnetic field between the first and second magnets; said magnetic field adapted to substantially encompass said perishable substance; and a porous material located between the first and second magnets to prevent contact between the first and second magnets.

2. A container as defined in claim 1, wherein the porous material is adapted to surround the perishable material.

3. A container as defined in claim 1, wherein the porous material is selected from the group including a gauze and a porous plastic.

4. A container made of a substantially dielectric material adapted to hold a perishable substance comprising:
- a container portion having an opening therein adapted for releasing the perishable substance;
- a first magnet supported on one side of the container portion; p1 a second magnet supported on an opposite side of the container portion relative to the first magnet defining a magnetic field between said first and second magnets, said first and second magnets having a length extending in the longitudinal direction of the container portion which is greater than the width of said magnets, whereby said magnetic field is adapted to substantially encompass a perishable substance within the container; and
- means for moving at least one magnet relative to the other magnet.

5. A container as defined in claim 4, wherein the means for moving includes a flexible, tubular portion defined by the container portion, and coupled to at least one of the first and second magnets for movement of at least one of the first and second magnets with movement of the flexible, tubular portion.

* * * * *